(12) United States Patent  (10) Patent No.: US 8,734,628 B2
Casasanta, III  (45) Date of Patent: May 27, 2014

(54) MICROFLUIDIC CHANNEL DEVICE WITH ARRAY OF DRIVE ELECTRODES

(75) Inventor: Vincenzo Casasanta, III, Woodinville, WA (US)

(73) Assignee: Empire Technology Development, LLC, Wilmington, DE (US)

( * ) Notice: Subject to any disclaimer, the term of this patent is extended or adjusted under 35 U.S.C. 154(b) by 519 days.

(21) Appl. No.: 12/720,755

(22) Filed: Mar. 10, 2010

(65) Prior Publication Data

US 2011/0220504 A1  Sep. 15, 2011

(51) Int. Cl.
*G01N 30/00* (2006.01)
*B01D 57/02* (2006.01)

(52) U.S. Cl.
USPC ....... 204/450; 204/600; 422/68.1; 422/82.01; 435/287.1; 73/61.52; 210/656; 210/198.2; 210/635

(58) Field of Classification Search
USPC .............. 204/450, 400, 600; 422/82.01, 68.1; 435/287.1; 73/61.52; 210/198.2, 656, 210/635
See application file for complete search history.

(56) References Cited

U.S. PATENT DOCUMENTS

| | | | |
|---|---|---|---|
| 6,911,132 B2 | 6/2005 | Pamula et al. | |
| 7,217,367 B2 | 5/2007 | Huang et al. | |
| 2004/0031688 A1 | 2/2004 | Shenderov | |
| 2004/0058423 A1* | 3/2004 | Albritton et al. | 435/173.7 |
| 2006/0165565 A1* | 7/2006 | Ermakov | 422/130 |
| 2007/0020689 A1* | 1/2007 | Caracci et al. | 435/7.1 |
| 2007/0241068 A1 | 10/2007 | Pamula et al. | |
| 2008/0050834 A1* | 2/2008 | Pamula et al. | 436/86 |
| 2008/0053205 A1* | 3/2008 | Pollack et al. | 73/61.71 |
| 2008/0110753 A1 | 5/2008 | Fourrier et al. | |
| 2008/0210558 A1* | 9/2008 | Sauter-Starace et al. | 204/450 |
| 2008/0230386 A1* | 9/2008 | Srinivasan et al. | 204/450 |
| 2008/0247920 A1* | 10/2008 | Pollack et al. | 422/243 |

FOREIGN PATENT DOCUMENTS

| | | |
|---|---|---|
| CN | 101031362 A | 9/2007 |
| CN | 101146595 A | 3/2008 |
| CN | 101400993 A | 4/2009 |
| CN | 101430299 A | 5/2009 |
| CN | 101501488 A | 8/2009 |

(Continued)

OTHER PUBLICATIONS

Miller, Chromatography, second edition, 2005.*

(Continued)

*Primary Examiner* — Jennifer Dieterle
(74) *Attorney, Agent, or Firm* — Moritt Hock & Hamroff LLP; Steven S. Rubin, Esq.

(57) ABSTRACT

Technologies are generally described for microfluidic channel devices. Some example devices may include a substrate having a substrate surface, with an array of drive electrode assemblies disposed upon the substrate surface. The drive electrode assemblies may be arranged along a path. Each drive electrode assembly may include one or more of a drive electrode layer, a dielectric layer and/or a stationary phase layer. The device may further include a plate including a plate surface. The device may further include a reference electrode configured on the plate surface to face the stationary phase layer of the drive electrode assemblies and separated from the substrate surface by a distance. The device may further include a voltage source effective to output a voltage potential, the voltage source configured in communication with the drive electrode assembly and the reference electrode. The device may further include an electrode selector effective to control the voltage source.

24 Claims, 7 Drawing Sheets

(56) References Cited

FOREIGN PATENT DOCUMENTS

| | | |
|---|---|---|
| CN | 1964788 A | 11/2013 |
| JP | 2005030525 | 3/2005 |
| JP | 2008502882 | 1/2008 |
| JP | 2009534653 A | 9/2009 |
| WO | 2006003293 A2 | 1/2006 |
| WO | 2006000469 A1 | 5/2006 |
| WO | 2006046988 A1 | 5/2006 |
| WO | 2006081558 A2 | 8/2006 |

OTHER PUBLICATIONS

"Electrowetting-based actuation of liquid droplets for microfluidic application"; Pollack et al., App. Phys. Lett. 77 (2000) 1725.

"Scalable fabrication of electrowetting displays with self-assembled oil dosing"; Sun et al., Appl. Phys. Lett. 91 (2007) 11106.

"A full description of a simple and scalable fabrication process for electrowetting displays", Zhou et al., J. Micromech. Microeng. 19 (2009) 65029.

"Creating, Transporting, Cutting, and Merging Liquid Droplets by Electrowetting-Based Actuation for Digital Microfluidic Circuits"; Cho et al., J. MEMS 12 (2003) 70.

"Electrowetting: from basics to applications"; Mugele et al., J. Phys: Condens. Matter 17 (2005) R705.

"Electrowetting and electrowetting-on-dielectric for microscale liquid handling"; Lee et al., Sensors and Actuators A 95 (2002) 259.

Digital Microfluidics, http://microfluidics.ee.duke.edu, downloaded, Mar. 4, 2010.

PCT International Search Report PCT/ISA/210 for PCT/US2011/025244 dated May 12, 2011.

PCT Written Opinion of the International Searching Authority PCT/ISA/237 for PCT/US2011/025244 dated May 12, 2011.

Fair, "Digital Microfluidics: is a true lab-on-a-chip possible?"; Microfluid Nanofluid (2007) 3: 245-281.

Pan X. et al., A novel magnetic chromatographic microsystem, Journal of Functional Materials and Devices, Apr. 2008, 5 pages, vol. 14, No. 2.

Kameoka, J. et al., A Polymeric Microfluidic Chip for CE/MS Determination of Small Molecules, Anal. Chem. 2001, 1935-1941, 73.

Rios, A. et al., Challenges of analytical microsystems, Trends in Analytical Chemistry, 2006, 467-479, vol. 25, No. 5.

Fair, R.B., Digital microfluidics: is a true lab-on-a-chip possible?, Mlcrofluid Nanofluid, 2007, 245-281.

\* cited by examiner

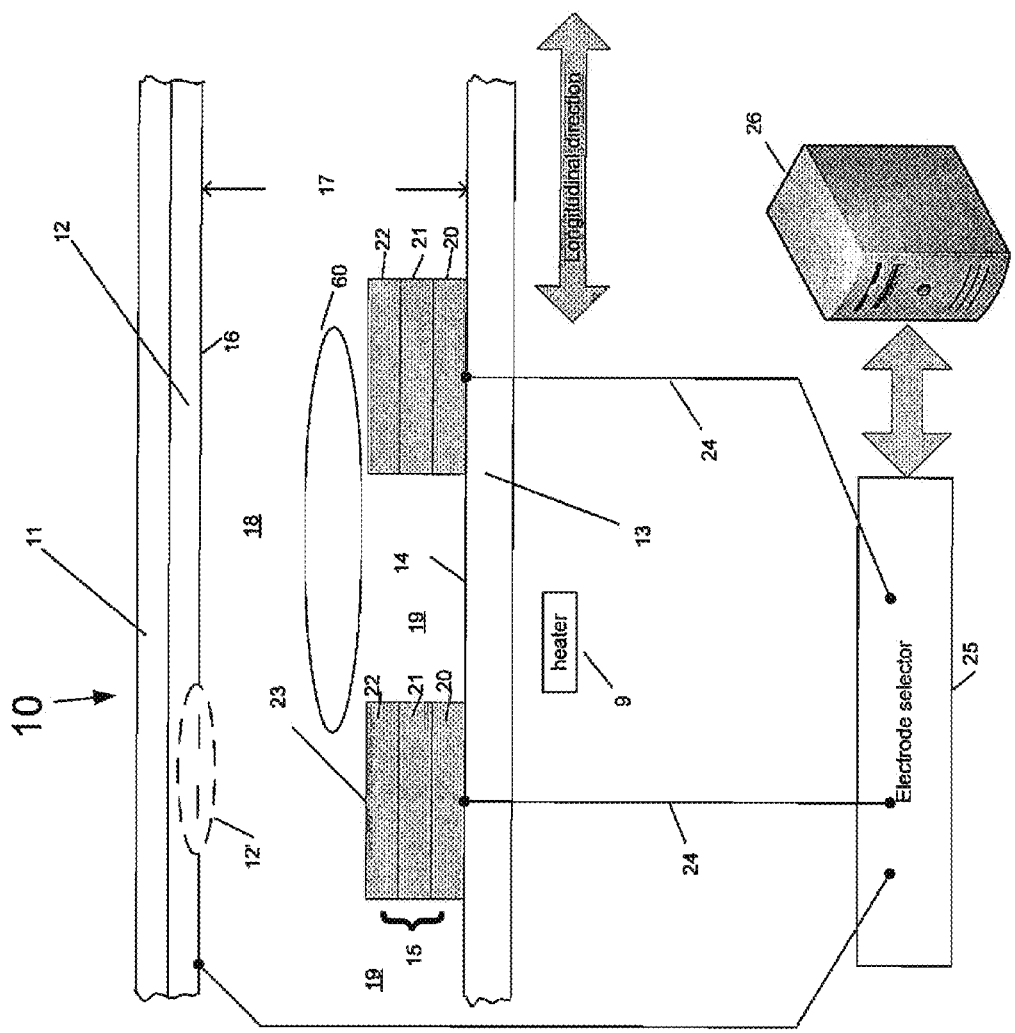

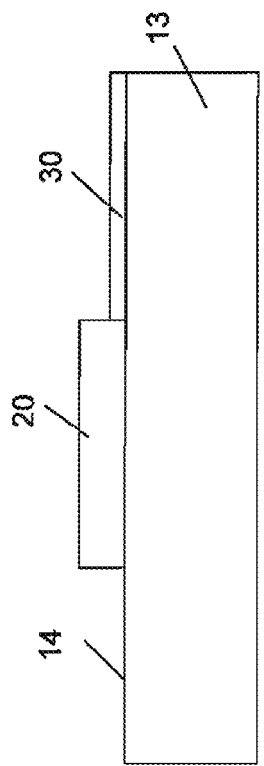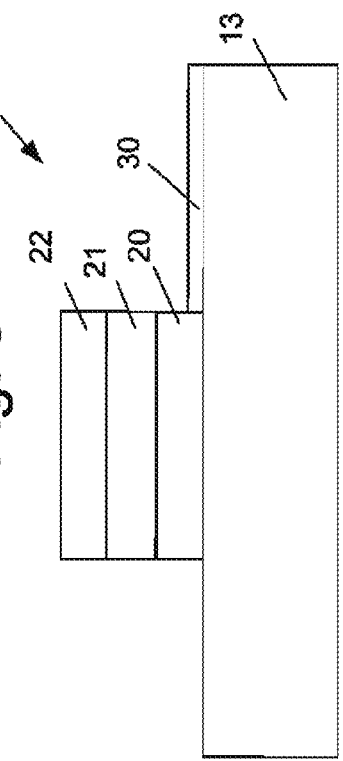

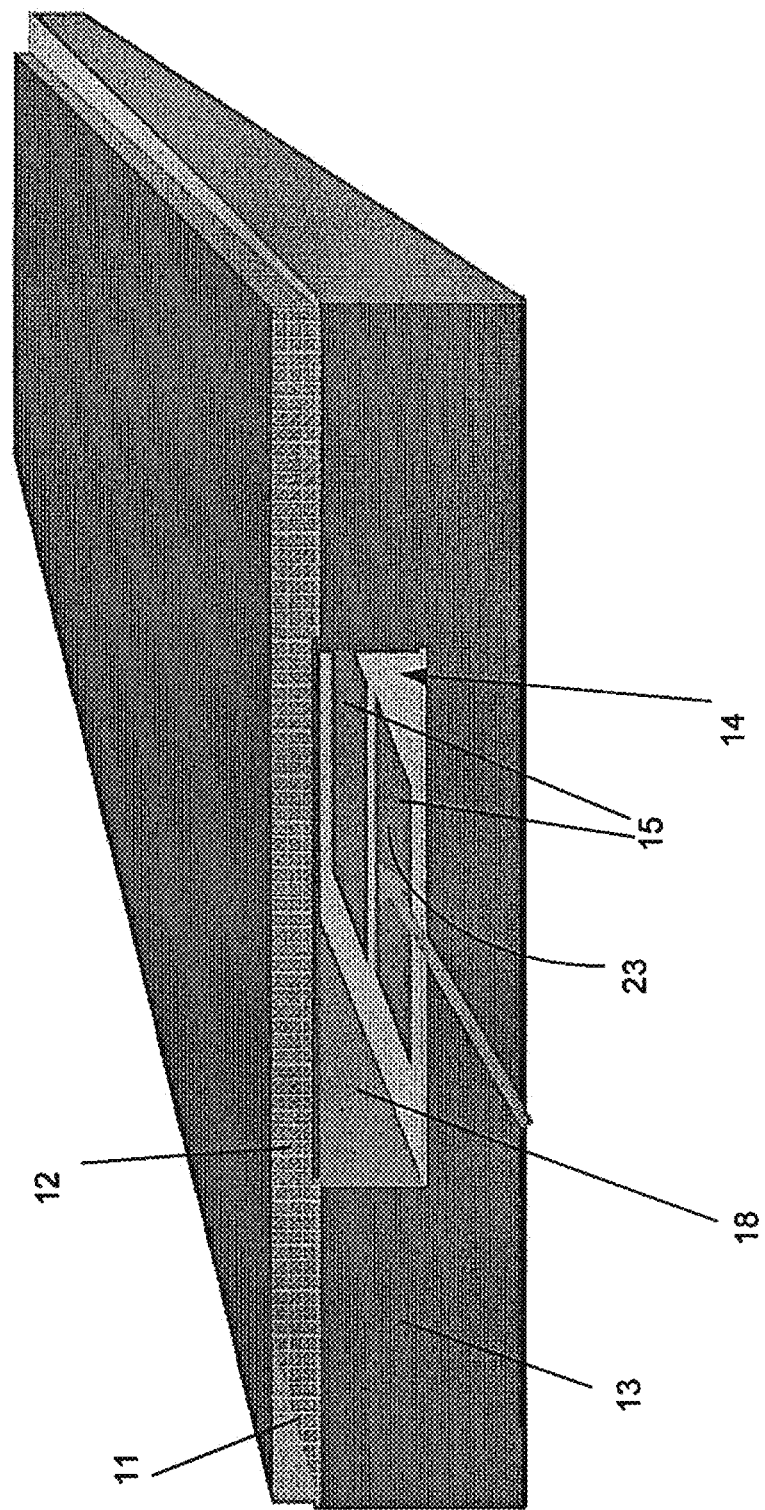

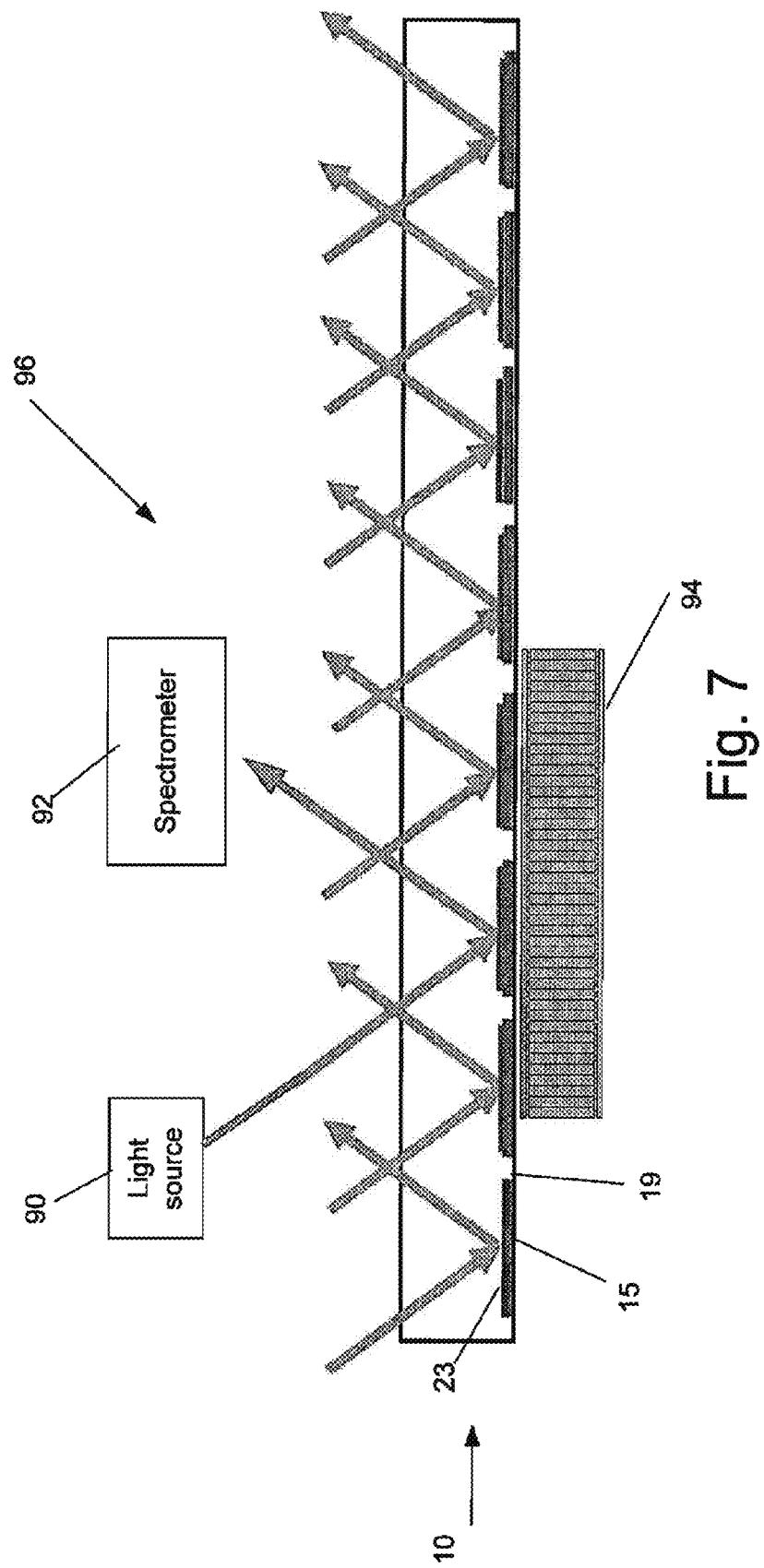

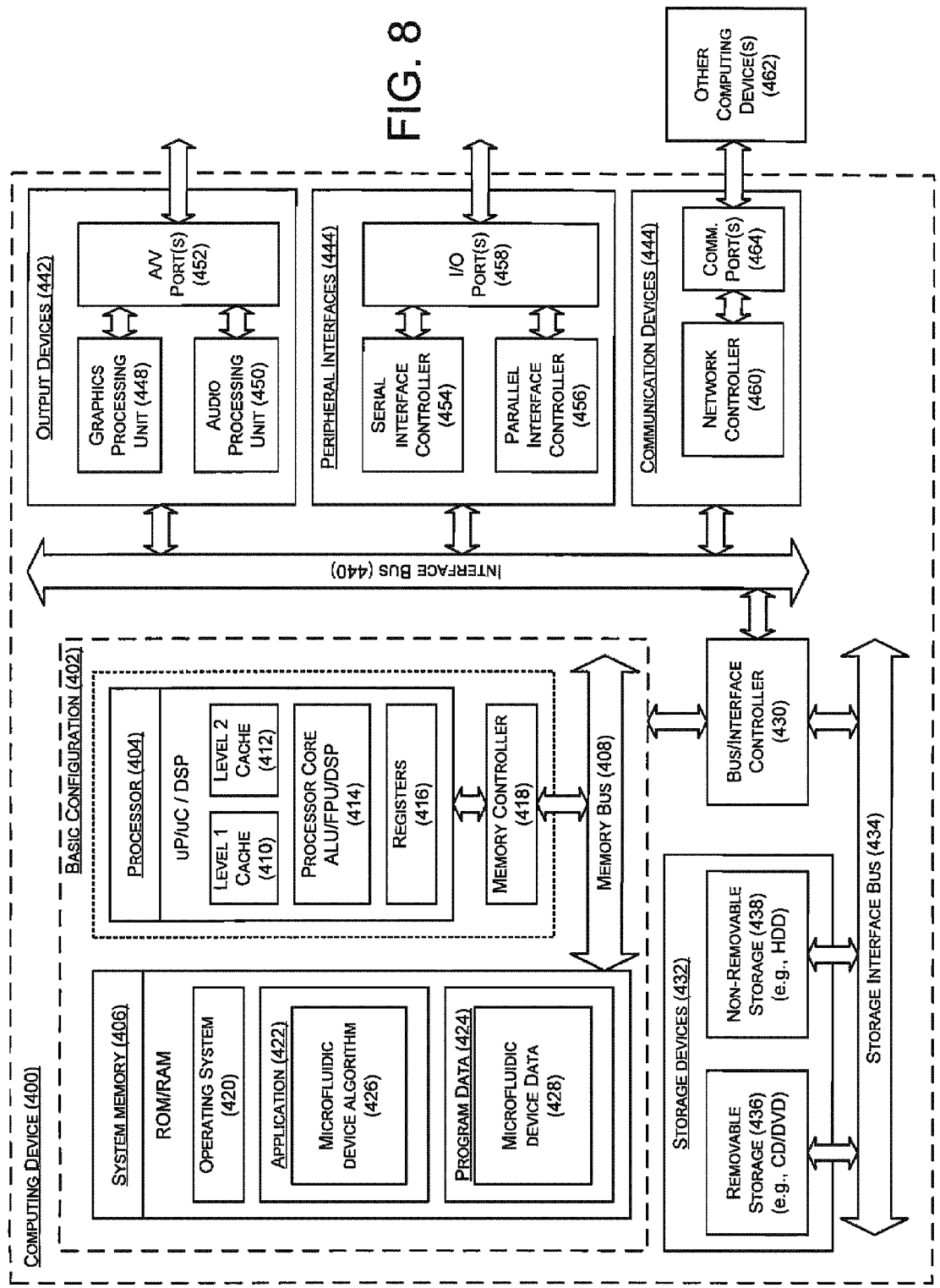

MICROFLUIDIC CHANNEL DEVICE WITH ARRAY OF DRIVE ELECTRODES

BACKGROUND

Unless otherwise expressly indicated herein, none of the material presented in this section is prior art to the claims of this application and is not admitted to be prior art by having been included herein.

Microchemical reactors may be used as platforms for chemical discovery and synthesis. Many reactors rely on microfluidic channel and "lab-on-a-chip" concepts. Fluids are commonly transported through such devices by capillary action, micro-pumps or electro-kinetic actuation. In synthetic chemistry, separation, isolation and identification of reaction product(s) are often accomplished by various methods of chromatography ranging from simple paper chromatography and thin layer chromatography (referred to as "TLC") to advanced high pressure liquid chromatography (referred to as "HPLC").

BRIEF DESCRIPTION OF THE FIGURES

The foregoing and other features of this disclosure will become more fully apparent from the following description and appended claims taken in conjunction with the accompanying drawings. Understanding that these drawings depict only some embodiments in accordance with the disclosure and are therefore not to be considered limiting of its scope, the disclosure will be described with additional specificity and detail by reference to the accompanying drawings in which:

FIG. 1 is a side cross-sectional schematic view of a microfluidic channel device;

FIGS. 2, 3 and 4A-E are schematic illustrations of stages in the construction of a microfluidic channel device;

FIG. 5 is a perspective view of a microfluidic channel device;

FIG. 7 is a schematic illustration of an analytical system; and

FIG. 8 is a block diagram illustrating an example computer device that is arranged to control a microfluidic channel device;

Figure 4A:
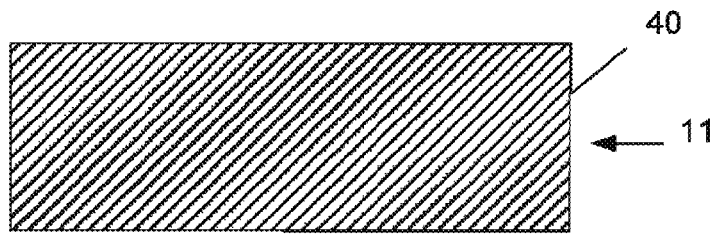
Figure 4B:
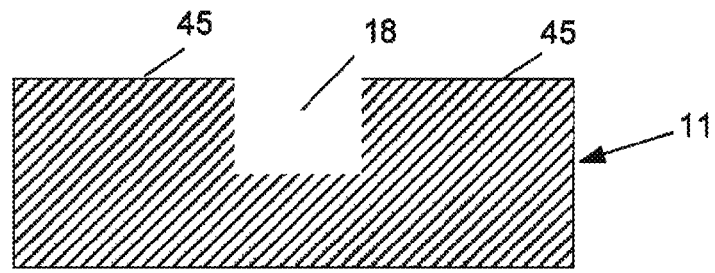

all arranged according to at least some embodiments described herein.

DETAILED DESCRIPTION

In the following detailed description, reference is made to the accompanying drawings which form a part thereof. In the drawings, similar symbols typically identify similar components unless context indicates otherwise. The illustrative embodiments described in the detailed description, drawings and claims are not meant to be limiting. Other embodiments may be utilized and other changes may be made without departing from the spirit or scope of the subject matter presented herein. It will be readily understood that the aspects of the present disclosure as generally described herein and as illustrated in the accompanying figures can be arranged, substituted, combined, separated and/or designed in a wide variety of different configurations all of which are explicitly contemplated herein.

This disclosure is generally drawn, inter alia, to apparatuses, systems, devices and methods relating to a microfluidic channel device for separating and/or analyzing small volumes of chemical products.

Briefly stated, technologies are generally described for microfluidic channel devices. Some example devices may include a substrate having a substrate surface, with an array of drive electrode assemblies disposed upon the substrate surface. The drive electrode assemblies may be arranged along a path. Each drive electrode assembly may include one or more of a drive electrode layer, a dielectric layer and/or a stationary phase layer. The device may further include a plate including a plate surface. The device may further include a reference electrode configured on the plate surface to face the stationary phase layer of the drive electrode assemblies and separated from the substrate surface by a distance. The device may further include a voltage source effective to output a voltage potential, the voltage source configured in communication with the drive electrode assembly and the reference electrode. The device may further include an electrode selector effective to control the voltage source.

As discussed in more detail below, a microfluidic channel device may include a planar array of drive electrodes within a microfluidic channel, where the planar array of drive electrodes are configured to produce an electrowetting effect. A voltage potential difference may be applied in a desired sequence to achieve liquid droplet movement along the length of the microfluidic channel. The microfluidic channel device described herein may be adapted for use in a stand-alone microchromatograph device or system. In some examples, the microfluidic channel device may be integrated into a microfluidic lab-on-a chip device or system.

FIG. 1 is a side cross-sectional schematic view of a microfluidic channel device in accordance with at least some embodiments herein. A microfluidic channel device 10 may be used in a microfluidic planar chromatograph such as that illustrated in FIGS. 6A-C. Microfluidic channel device 10 includes a plate 11, a reference electrode 12 configured in contact with plate 11 and including a surface 16, a substrate 13 including a surface 14, an array of drive electrode assemblies 15 configured in adherent contact with surface 14, and a heater 9.

In some examples, microfluidic channel device 10 includes plate 11 but does not include reference electrode 12. In other examples, microfluidic channel device includes reference electrode 12 but does not include plate 11. Surface 16 of reference electrode 12 may be separated from surface 14 of substrate 13 by a predetermined distance 17 defining the height dimension of microfluidic channel 18. A size of distance 17 may be adjusted by moving reference electrode 12 and substrate 13. For example, if a reaction changes a volume of an analyte (discussed in more detail below) a size of distance 17 may be adjusted accordingly. Channel 18 may define any type of cross-sectional shape. In some examples, channel 18 may define a cross-section that is square, rectangular, elliptical, racetrack, oval, diamond, hexagonal, circular, and concentric circles, etc. In some examples, reference electrode 12 and drive electrode assemblies 15 extend parallel to one another and have the same cross-sectional shape.

The height and width dimensions of microfluidic channel 18 may be configured to accommodate a droplet 60 containing analytes for separation. For example channel 18 may have a width of about 10 μm to about 5 mm; a height of about 1 μm to about 5 mm; and a length of about 0.5 mm to about 50 mm.

An array of spaced-apart drive electrode assemblies 15 may be disposed upon surface 14 of substrate 13 to define the length or longitudinal direction of microfluidic channel 18. In some examples, each drive electrode assembly 15 may have a height of about 1.01 μm to about 2 mm. Gap spaces 19 between each drive electrode assembly 15 may be arranged substantially co-planar with the drive electrode assemblies 15. In some examples, gap spaces 19 may extend about 0.5 μm to about 50 μm, In some examples, gap spaces 19 may be filed with an electrically insulating material such as an optically translucent material. Each drive electrode assembly 15 may be configured adjacent to at least one of gap spaces 19. Each drive electrode 15 may include a drive electrode layer 20, an intermediate dielectric layer 21, and a stationary phase layer 22. A surface 23 of stationary phase layer 22 may be configured to face microfluidic channel 18 and reference electrode 12. A distance between surface 23 and surface 16 may be adjusted as desired for varying thicknesses in a single elution.

Plate 11 and substrate 13 may be fabricated from the same or different chemically inert material(s), e.g., glass(es), ceramic(s), polymer(s), etc., combinations thereof, and the like. Representative glasses include, without limitation, silicates, borosilicates and aluminosilicates. Representative ceramics include, without limitation, $Al_2O_3$ in various purities, nitrides such as $Si_3N_4$, SiON and AlN. Representative polymers include, without limitation, polyacrylates, polystyrene, polycarbonate, polyamides, polyimides and epoxies. Substrate 13 may also include silicon with patterned oxide, nitride, or polymer channels. Alternatively, microfluidic channel 18 may be etched onto surface 14 of substrate 13.

In some examples, a fluid channel 18 may be formed on the surface of substrate 13. As discussed above, channel 18 may be, in some examples, linear or circular in cross-section and may have branching points such that droplet 60 may be moved and turned through adjustment of voltages. The length of microfluidic channel 18 may be a function of the desired resolution of an associated planar chromatograph Longer channels may produce higher resolutions. In examples including lab-on-a chip architectures, the length of microfluidic channel 18 may range from about 1 mm to about 10 cm and the width of the microfluidic channel 18 may range from about 10 microns to about 5 mm.

As shown in FIG. 1, planar array of drive electrode assemblies 15 may be patterned onto surface 14 of substrate 13. Various techniques may be used to create drive electrode assemblies 15. For example, drive electrode layer 20 may be vapor-deposited as a thin film by evaporation or sputtering. Alternatively, drive electrode layer 20 may be deposited by any of several suitable electroplating techniques. Drive electrode layer 20 may be patterned by photolithographic, lift off, etching or shadow mask methods. Drive electrode layer 20 may be fabricated from any suitable metal. The selection of the metal may depend upon the ability of the metal to satisfactorily adhere to dielectric layer 21, which may be subsequently formed on the metal. The metal constituting the drive electrode layer 20 need not be chemically inert since dielectric layer 22 will isolate drive electrode layer 20 from the mobile phase and the analytes Metals that may be used for providing drive electrode layer 20 may include, without limitation, aluminium (Al), copper (Cu), gold (Au), nickel (Ni), silver (Ag), platinum (Pt), titanium (Ti) and their alloys. Depending upon the deposition method, in some examples, dimensions of drive electrode layer 20 may be: width—about 10 μm to about 5 mm; thickness—about 10 nm to about 1 μm; length—about 10 μm to about 1 mm.

Onto the surface of each metal electrode layer 20 may be an intermediate layer 21 that can be implemented as a dielectric adhesion layer. Dielectric adhesion layer 21 may serve two purposes: as a dielectric layer disposed between the mobile phase and each drive electrode layer 20, and as a chemical adhesion layer disposed between each drive electrode layer 20 and each stationary phase layer 22. The composition and the thickness of dielectric adhesion layer 21 may be tailored as desired to serve as a chemical linkage or physical bonding between drive electrode layer 20 and each stationary phase layer 22 as well as an insulator between the latter two layers. Various organic and/or inorganic materials may be utilized for the construction of dielectric adhesion layer 21. Representatives of such materials include organic polymers such as polysilanes, polyacrylates and polyimides and inorganic materials such as oxides and nitrides. In some examples, the thickness of dielectric adhesion layer 21 may range from about 1 nm to about 1000 nm.

Stationary phase layer 22 may be formed from any of the materials that are useful as the stationary phase in thin layer chromatography (TLC) or high performance liquid chromatography (HPLC). In some examples, a thickness of stationary phase layer 22 may be about 1 μm to 1 mm. A representative stationary phase layer can be fabricated from such materials as, without limitation, functionalized silica particles, highly engineered gels, hydrogels, polymers such as polyacrylimide, nanoparticle assembles and porous particulate dispersions. The selection of a specific material for stationary phase layer 22 may be based on the nature of the analytes to be separated. Various properties of the analytes may be taken into consideration when choosing the material for stationary phase layer 22 including, without limitation, the polarity, charge and molecular size of the analytes. Depending upon the type of separation desired, stationary phase layer 22 may function in accordance with any desired separation mechanism including, without limitation, normal or reverse phase configurations, binding affinity, ion exchange or size exclusion. In some examples, different types of material may be used for stationary phase layers 22 in a single device 10. For example, a material of a first stationary phase layer 22 may be chosen based on size exclusion and a material of a second stationary phase layer 22 may be chosen based on binding affinity Still referring to FIG. 1, a reference electrode 12 may be disposed upon the surface of plate 11 in a configuration that faces surface 14 of substrate 13. In some examples, and as shown in FIG. 1, reference electrode 12 may be provided as a single continuous layer disposed upon the surface of plate 11 and shared by all planar-arrayed drive electrode assemblies 15. In other examples, reference electrode 12 may comprise an array of spaced-apart reference electrode units 12' that may be disposed upon plate 11, each reference electrode 12' facing a corresponding drive electrode assembly 15. In some examples, a continuous reference electrode 12 may provide single fast elution whereas discontinuous electrode units 12' may allow branching into other channels and may compensate for droplet shape changes during elution. For example, when a droplet goes through channel 18, analytes in the droplet may be eluted gradually. This can cause a surface tension change and/or a charge/polarity change on the droplet. A potential across reference electrode 12' and the drive electrode 15 may be adjusted accordingly to control the shape and, therefore, the movement of the droplet. Reference electrode 12 may be optically translucent. In some examples, both plate 11 and reference electrode 12 may be optically translucent in order to allow the detection and/or identification of the separated analytes as described in detail below.

Reference electrode 12 may be fabricated from a translucent conductor material such as indium tin oxide (ITO), tin oxide ($SnO_2$) or zinc oxide (ZnO). In some examples, the thickness of reference electrode 12 may range from about 100 nm to about 10 μm. Reference electrode 12 may be configured to establish an adjusting voltage potential across microfluidic channel 18, which can modify the contact angle and the surface tension of sample droplet 60. For example, by changing the adjusting voltage potential, device 10 may move, deform, compress/elongate, confine and/or shape the sample droplet 60 introduced into microfluidic channel 18. When sample droplet 60 is driven over stationary phase layer 22 of each drive electrode assembly 15 along the length of microfluidic channel 18, various analytes may be removed from sample droplet 60. Such analytes may diffuse within and be immobilized on stationary phase layer 22. This diffusion may lead to polarity changes in the analyte-depleted sample droplet. In order to maintain the electrowetting-caused movement of the sample droplet, shape modification of the droplet may be desirable as the sample droplet undergoes polarity changes.

A microfluidic channel device in accordance with the disclosure may include multiple microfluidic channels in communication with one another. Such a structure may provide for branching of a droplet to multiple channels facilitating secondary elution and/or separation. The microfluidic channel may be filled with a surrounding medium. A viscosity of the medium may be chosen to allow for introduction and equilibration. In some examples, the surrounding medium and the mobile phase may be immiscible. Any suitable pairing of organic and/or aqueous solvents may be used for the surrounding medium and the mobile phase. For example, the surrounding medium and the mobile phase may be independently hydrophobic, hydrophilic, aqueous, non-aqueous, polar or non-polar. In some examples, the mobile phase may be oil-based and the surrounding medium may be water.

An adjusting voltage between the drive electrode 20 having same droplet 60 in proximity therewith and reference electrode 12 may be used in order to allow the sample droplet to change shape and be displaced. This may allow droplet 60 to be moved along drive electrode 12 as a result of the electrowetting effect. When the sample droplet and the surrounding medium have contrasting polarity, deformation of the droplet may occur. In these examples, the surface tension of the droplet may be adjusted. For example, when using hexane as the mobile phase and deionized (DI) water as the surrounding medium, surface tension of the droplet may be adjusted by the introduction of surfactants into the surrounding medium. In some examples, the mobile phase may be polar and the surrounding medium may be ambient air. In some examples, the mobile phase may be polar and the surrounding medium may be an evacuated cavity. In some examples, the mobile phase may be non-polar and the surrounding medium may be polar. Therefore, depending upon the nature of the analytes to be separated, various chromatography methods may be utilized (as in conventional HPLC) in which the polarity contrasts between the mobile phase and the surrounding medium may be adjusted to achieve desired separation rates and resolution. Heater 9 may be arranged to provide heat to channel 18 and thereby adjust a viscosity of the mobile phase, and/or a binding affinity of the stationary phase. Again, referring to FIG. 1, reference electrode 12 and drive electrode layer 20 of each drive electrode assembly 15 may be in communication with an electrode selector 25 via electrical connectors 24. Electrode selector 25 may control voltage inputs, timings and durations to drive electrode assembly 15 and reference electrode 12. In some examples, electrode selector 25 may be controlled by a controller, a processor or a computer 26.

FIGS. 2, 3 and 4A-E are schematic illustrations of stages in the construction of a microfluidic channel device in accordance with at least some embodiments herein.

Referring to FIG. 2, surface 14 of substrate 13 may be patterned with drive electrode layer 20. This patterning may be achieved by resist-based photolithography (e.g., positive or negative photoresist) and metals may be deposited on surface 14 via methods such as sputtering, evaporation or electroplating. Chemical etching and resist stripping may also be used to form the pattern on the surface 14 of the substrate 13. Drive electrode layer 20 may be patterned on the surface 14 of substrate 13 in any desired form. In some examples, drive electrode layers 20 may be patterned as a linear array of electrode pads (e.g., square, rectangular, round, elliptical) or some other suitable geometry. Each drive electrode layer may include an independent conductor trace 30 that is patterned on the surface 14 of substrate 13 to the exterior portions of the microfluidic channel assembly to facilitate external electrical connection.

Referring to FIG. 3, a layer of adhesive insulator material, i.e., dielectric adhesion layer 21, may be deposited upon the surface of drive electrode layer 20. The deposition of the adhesive dielectric layer 21 can be accomplished by, for example, low temperature chemical vapor deposition of oxides or by spin, dip, screen print or vapor coating of organics or polymers. Dielectric adhesion layer 21 may be deposited over the entire surface of drive electrode layer 20 as shown in FIG. 3. In some examples, the thickness of dielectric adhesion layer 21 may be in a range from about 1 nm to about 1000 nm.

Stationary phase layer 22 may be applied to or formed upon the surface of dielectric adhesion layer 21 to complete drive electrode assembly 15. Stationary phase layer 22 may enable one or more microfluidic channels to have a chromatographic function. Stationary phase layer 22 may be in a range of thickness from about 10 nm to about 10 μm. In the manner described above, an example substrate assembly 35 may be produced.

Referring to FIGS. 4A-4E, starting with a monolithic slab 40 of selected construction material as shown in FIG. 4A, planar-surfaced microfluidic channel 18 can be formed therein by such microfabrication techniques as chemical etching, plasma/reactive ion dry etching, mechanical machining, electrical discharge machining, laser machining, molding, imprinting, lithographic patterning or any other suitable manufacturing technique. These example techniques may be utilized to provide plate 11 with microfluidic channel 18 in the configuration illustrated in FIG. 4B. In some examples, the length of microfluidic channel 18 may be in a range from about 1 mm to about 10 cm, the width of microfluidic channel 18 may be in a range from about 10 μm to about 5 mm and the height, or depth, of microfluidic channel 18 may be in a range from about 10 μm to about 5 mm.

Figure 4C:
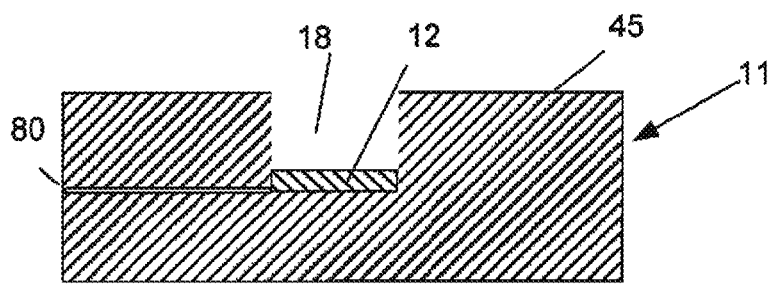

As shown in FIG. 4C, reference electrode 12 may be deposited upon the surface of plate 11 by vapor or sputter deposition methods. Reference electrode 12 may be in a range in thickness (depth) from about 1 nm to about 1000 nm and may include a trace conductor 80 that is configured to the exterior of the plate 11.

Figure 4D:
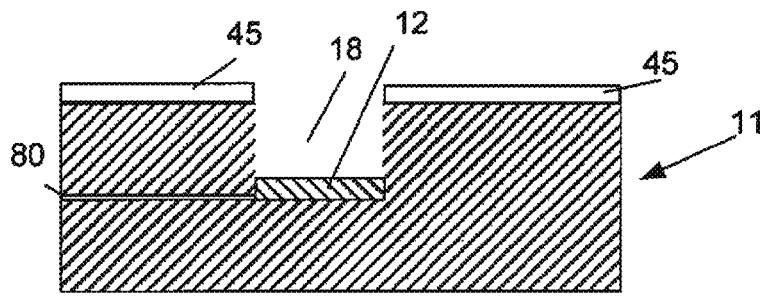
Figure 4E:
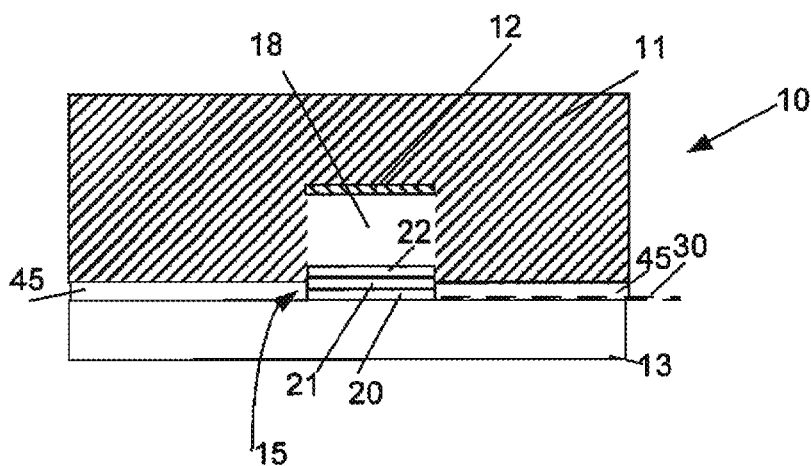

In FIG. 4D, an adhesive layer 45 may be applied to the non-channeled portions of plate 11. Various types of automatic fluid dispensing equipment may be used for the application of adhesive layer 45. In some examples, the application of the adhesive layer may be carried out using a robotic syringe adhesive dispenser. Plate 11 with adhesive 45 may then be inverted and bonded to substrate assembly 35 such that reference electrode 12 is configured to face drive electrode assembly 15 as shown in FIG. 4E. Some examples of adhesives that may be used in this bonding procedure include, without limitation, epoxy resins, polyvinyl acetate, polyurethane and cyanoacrylate polymers.

FIG. 5 is a perspective view of a microfluidic channel device in accordance with at least some embodiments herein. As shown in the example, the array of drive electrode assemblies 15 may be patterned in a linear fashion upon the surface 14 of substrate 13. Opposite the drive electrode assemblies 15 is reference electrode 12. The arrow represents the introduction of a sample droplet of analytes into microfluidic channel 18.

Figure 6A:
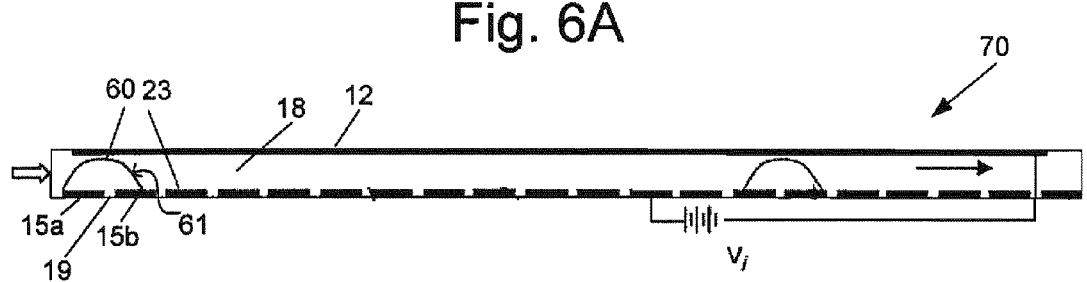
FIG. 6A is side cross-sectional schematic view of a planar microchromatograph incorporating a microfluidic channel device.
Figure 6B:
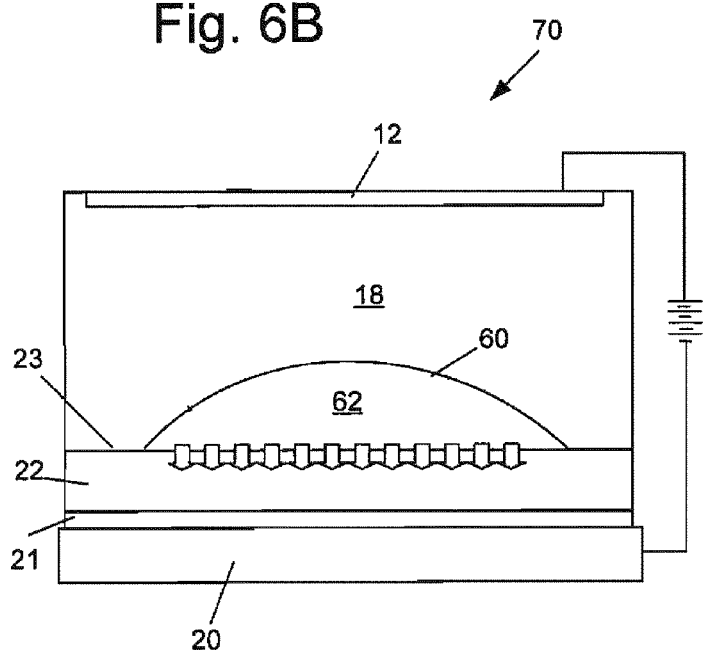
FIG. 6B is side cross-sectional schematic view of a planar microchromatograph incorporating a microfluidic channel device.
Figure 6C:
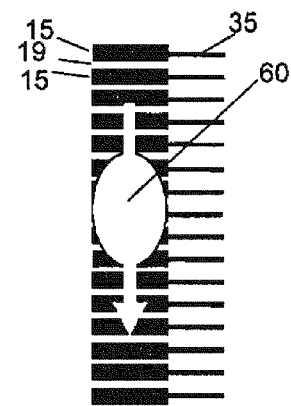
FIG. 6C is a top plan schematic view of a planar microchromatograph incorporating a microfluidic channel device.

FIG. 6A is side cross-sectional schematic view of a planar microchromatograph incorporating a microfluidic channel device in accordance with at least some embodiments herein. FIG. 6B is front/back cross-sectional schematic view of a planar microchromatograph incorporating a microfluidic channel device in accordance with at least some embodiments herein. FIG. 6C is a top plan schematic view of a planar microchromatograph incorporating a microfluidic channel device in accordance with at least some embodiments herein.

Referring to FIGS. 6A, 6B and 6C, after a chemical reaction has been carried out in a suitable microchemical reactor or other external reactor, a sample of the reaction product containing analytes to be separated may be transferred to microfluidic channel 18. The transfer may be performed by any suitable means, e.g., a micropipette, to the inlet port of microfluidic channel 18 and onto the first drive electrode assembly 15 in the array. The mobile phase may be mixed with the product sample to produce sample droplet 60. Mixing of mobile phase and analytes may be accomplished by electrowetting-induced mixing. Once mixing is complete, droplet 60 may be moved along drive electrode assemblies 15 by voltage-induced motion, i.e., the electrowetting effect, as further described below.

A motion of sample droplet 60 may be produced by static and/or periodic potentials that are applied between reference electrode 12 and drive electrode layer 20, hereinafter designated $V_j$. A surface tension differential on one side of droplet 60 can be produced by application of voltage $V_j$ adjacent to the meniscus 61 of droplet 60 where motion is desired. At the same time, a voltage potential towards the interior 62 of droplet 60 may be maintained either at zero voltage or a voltage lower than $V_j$.

The described voltages can be regulated relative to a potential associated with reference electrode 12. Successive application of voltage potentials on adjacent drive electrode layers 20 can result in droplet 60 being driven along the path defined by the drive electrode assembly array.

According to some examples as shown in FIGS. 6A and 6B, sample droplet 60 may be disposed on the first of drive electrode assemblies 15 in the array. Droplet 60 may partially overlap an adjacent drive electrode assembly 15 with intervening gap space 19 disposed between the first and the second drive electrode assemblies 15a, 15b in the array. Voltages may be applied to the first and second drive electrode layers in assemblies 15a, 15b to spread at least a portion of droplet 60 across the second electrode assembly 15b. The voltage on the first drive electrode assembly 15a may then be deactivated or reduced to move the sample droplet 60 from the first drive electrode assembly 15a to the second drive electrode assembly 15b in the array and in like manner to successive drive electrode assemblies in the array.

The surface tension responsible for producing the forces involved may be dictated by the following equation, $$\gamma(V) = \gamma(0) \cdot \frac{1}{2}CV^2$$

Where $\gamma(V)$ is the surface tension of a droplet at an electrode pad with a particular applied voltage V and $\gamma(0)$ is the surface tension without an applied voltage. The capacitance per unit surface area between droplet 60 and underlying electrode 15 is denoted as C, which is a composite value comprised of the capacitance of the insulator/adhesion layer 21 and the capacitance of the stationary phase 22.

The surface tension without applied voltage, $\gamma(0)$, relies on one or more variables including, without limitation, the polarity of the solvent in the mobile phase, the concentration and species of the analytes, the composition and structure of stationary phase layer 22, and/or the polarity of the surrounding medium in microfluidic channel 18. One or more of these variables may be, in turn, determined by the nature of the samples to be analyzed, the composition of the mobile and the stationary phases, and the type of the separation desired. In some examples, the initial surface tension $\{\gamma(0)\text{'s}\}$ may be within the range of from about 10 dyne/cm to about 100 dyne/cm and the voltages used in moving droplet 60 along microfluidic channel 18 may be within the range of from about 5 V to about 100 V.

The voltages on each of the drive electrodes layers 20 and/or reference electrode 12 may be controlled by an electrode selector as shown in FIG. 1. The electrode selector may be controlled by a processor as also shown in FIG. 1. In some embodiments, the microprocessor may be a computer.

Various actuation voltage sequences may be used to control the sample droplet speed (e.g., the rate of movement through microfluidic channel 18) including the size and shape of the droplet across the drive electrode assembly array. The actuation voltage may vary in magnitude and pulse width. In some examples, droplet 60 could move at a speed of about 1 mm/hour to about 10 cm/hour. In some examples, droplet 60 could have a size of about 10 μm in diameter to about 5 mm in diameter. In some examples, droplet 60 may have a volume of about 1 pl to about 1 ml and a shape that is circle or long oval in cross-section. In some examples, actuation voltages can vary from about 1 μV to about 10V and have a pulse width of about 1 μsec to about 100 minutes. As droplet 60 moves across the array of drive electrode assemblies 15, the analytes may be eluted onto stationary phase layer 22. Sufficient time may be provided to allow droplet 60 to dwell, or remain, upon surface 23 of each stationary phase layer 22 long enough so that the respective fractions may diffuse from the mobile phase in the sample droplet and diffuse within and bind to stationary phase layer 22. In some examples, the dwell time could be from about 0.01 sec to about 100 minutes.

In operation, droplet 60 may be introduced onto a drive electrode assembly 15 in the array. An actuation of an adjacent drive electrode assembly may be delayed until respective fractions diffuse from the mobile phase of the droplet 60 and bind to stationary phase layer 22 of the drive electrode assembly. The time that a sample droplet passes through the microfluidic channel may be controlled by the time delay between the actuation voltages on adjacent drive electrodes assemblies. In addition, with the same mobile phase and stationary phase, chromatographic resolution may be adjusted by varying the dwelling time of the droplet on the drive electrode assemblies. Thus, microfluidic devices discussed herein provide great flexibility.

As previously indicated, reference electrode 12 may be fabricated from a translucent conductor, e.g., of ITO glass. In addition, microfluidic channel 18 may be reflective from its base due to the metal drive electrode Therefore, various optical detection or spectroscopic analysis methods may be used to observe the separation of the sample droplet and analyze various fractions immobilized within stationary phase layer 22.

FIG. 7 is a schematic illustration of an analytical system arranged according to at least some embodiments described herein. An analytical system 96 may include a light source 90, a spectrometer 92, microfluidic channel device 10 and an advancing mechanism 94. In some examples, light from a light source 90 in the UV (ultra-violet)-visible-near IR (infra-red) range of the spectrum may be incident upon drive electrode assembly 15. The light may glance electrode assembly 15 at any angle entering and exiting from transparent reference electrode 12. Spectroscopy may be performed by a spectrometer 92 in accordance with any suitable technique, e.g., absorption spectroscopy or fluorescence spectroscopy both of which are described below.

Referring to FIGS. 1 and 7, absorption spectroscopy may be used to detect the fractionated analytes using a broadband light source from the UV to near-IR portions of the spectrum. In some examples that use absorption spectroscopy, plate 11 may be constructed of a translucent material and reference electrode 12 may be made of a translucent conductor such as ITO glass. A beam of input light, such as IR or UV generated by an IR or UV spectrometer, may be projected incident onto microfluidic channel 18. Correction for refraction from plate 11 and reference electrode 12 may be carried out by subtracting the intensity of the refracted light from the intensity of the incident light. The light intensity may be measured using photodiodes. After shining through transparent plate 11 and reference electrode 12, the broadband interrogation light may be projected onto stationary phase layer 22 of drive electrode assembly 15. The light reflected from the stationary phase layer may refract and exit from microfluidic channel 18 to spectrometer 92 positioned to collect the reflected light. Using spectrometer 92, a reference spectrum may be collected from stationary phase layer 22. In some examples, spectrometer 92 does not include eluted species on or within it. A sample spectrum may be collected from the stationary phase layer that contains eluted species. Using microprocessor 26, the reference spectrum may be subtracted from the sample spectrum to produce reflectance absorption spectra, which may then be used to identify the chemical species of the eluted analyte.

Fluorescence spectroscopy is similar to the absorption spectroscopy method discussed above. Light 90 with a narrow band (or from a laser) ranging from UV wavelengths to near-IR wavelength may be used. Spectrometer 92 may be used to obtain the fluorescence spectra of the analytes eluted onto stationary phase layer 22.

As shown in FIG. 7, drive electrode assembly 15 may be sequentially interrogated by system 96 using spectrometer 92. In other examples, microfluidic chromatograph assembly 70 can be moved by an advancing mechanism 94 to sequentially place each drive electrode assembly 15 under the spectrometer. For example, advancing mechanism 94 could include a shuttle using a solenoid or servo-motor.

FIG. 8 is a block diagram illustrating an example computing device 400 that is arranged to control a microfluidic device in accordance with at least some embodiments of the present disclosure. In a very basic configuration 402, computing device 400 typically includes one or more processors 404 and a system memory 406. A memory bus 408 may be used for communicating between processor 404 and system memory 406.

Depending on the desired configuration, processor 404 may be of any type including but not limited to a microprocessor (µP), a microcontroller (µC), a digital signal processor (DSP), or any combination thereof. Processor 404 may include one more levels of caching, such as a level one cache 410 and a level two cache 412, a processor core 414, and registers 416. An example processor core 414 may include an arithmetic logic unit (ALU), a floating point unit (FPU), a digital signal processing core (DSP Core), or any combination thereof. An example memory controller 418 may also be used with processor 404, or in some implementations memory controller 418 may be an internal part of processor 404.

Depending on the desired configuration, system memory 406 may be of any type including but not limited to volatile memory (such as RAM), non-volatile memory (such as ROM, flash memory, etc.) or any combination thereof. System memory 406 may include an operating system 420, one or more applications 422, and program data 424.

Application 422 may include a microfluidic device algorithm 426 that is arranged to perform the functions as described herein including those described previously with respect to FIGS. 1-7. Program data 424 may include microfluidic device data 428 that may be useful for a microfluidic device algorithm as is described herein. In some embodiments, application 422 may be arranged to operate with program data 424 on operating system 420 such that control of a microfluidic device may be provided. This described basic configuration 402 is illustrated in FIG. 6 by those components within the inner dashed line.

Computing device 400 may have additional features or functionality, and additional interfaces to facilitate communications between basic configuration 402 and any required devices and interfaces. For example, a bus/interface controller 430 may be used to facilitate communications between basic configuration 402 and one or more data storage devices 432 via a storage interface bus 434. Data storage devices 432 may be removable storage devices 436, non-removable storage devices 438, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and non-volatile, removable and non-removable media implemented in any method or technology for storage of information, such as computer readable instructions, data structures, program modules, or other data.

System memory 406, removable storage devices 436 and non-removable storage devices 438 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 400. Any such computer storage media may be part of computing device 400.

Computing device 400 may also include an interface bus 440 for facilitating communication from various interface devices (e.g., output devices 442, peripheral interfaces 444, and communication devices 446) to basic configuration 402 via bus/interface controller 430. Example output devices 442 include a graphics processing unit 448 and an audio processing unit 450, which may be configured to communicate to various external devices such as a display or speakers via one or more A/V ports 452. Example peripheral interfaces 444 include a serial interface controller 454 or a parallel interface controller 456, which may be configured to communicate with external devices such as input devices (e.g., keyboard, mouse, pen, voice input device, touch input device, etc.) or other peripheral devices (e.g., printer, scanner, etc.) via one or more I/O ports 458. An example communication device 446 includes a network controller 460, which may be arranged to facilitate communications with one or more other computing devices 462 over a network communication link via one or more communication ports 464.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 400 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 400 may also be implemented as a personal computer including both laptop computer and non-laptop computer configurations.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A microfluidic channel device including a microfluidic channel configured to receive and move a droplet, where the droplet includes at least two analytes, the microfluidic channel device comprising:
a substrate including a substrate surface;
an array of drive electrode assemblies disposed upon the substrate surface, the drive electrode assemblies being arranged along a path, each drive electrode assembly including:
a drive electrode layer including a first drive electrode surface configured in contact with the substrate surface and including a second drive electrode layer surface;
a dielectric layer including a first dielectric layer surface configured in contact with the second drive electrode surface and including a second dielectric layer surface and
at least one of the drive electrode assemblies includes a first stationary phase layer including a first stationary phase layer surface configured in contact with the second dielectric layer surface and including a second stationary phase layer surface, the first stationary phase layer comprising a first material configured to partition a first analyte from the droplet as the droplet is moved over the first stationary phase layer, so that at least some of the first analyte is separated from the droplet and the at least some of the first analyte remains partitioned in the first stationary phase layer when the droplet is moved from the first stationary phase layer;
a reference electrode configured to face the second stationary phase layer surface of the drive electrode assemblies and separated from the substrate surface by a distance defining the microfluidic channel; and
at least one of the drive electrode assemblies includes a second stationary phase layer including a first stationary phase layer surface configured in contact with the second dielectric layer surface and including a second stationary phase layer surface, the second stationary phase layer comprising a second material, different from the first material, the second material configured to partition a second analyte from the droplet as the droplet is moved over the second stationary phase layer, so that at least some of the second analyte is separated from the droplet and the at least some of the second analyte remains partitioned in the second stationary phase layer when the droplet is moved from the second stationary phase layer, and where the second analyte is different from the first analyte.

2. The device as recited in claim 1, wherein the drive electrode assemblies are arranged along a linear flow path.

3. The device as recited in claim 1, wherein the reference electrode is configured as a spaced-apart array of reference electrode units corresponding in number to a number of drive electrode assemblies in the array of drive electrode assemblies.

4. The device as recited in claim 3, wherein a surface of each reference electrode unit facing a corresponding drive electrode assembly corresponds to one or more of a square shaped electrode, a rectangular shaped electrode, a round shaped electrode or an elliptical shaped electrode.

5. The device as recited in claim 4, wherein a width of each of the reference electrode units and each of the drive electrode assemblies are about as wide as the microfluidic channel.

6. The device as recited in claim 1, wherein the reference electrode is optically translucent.

7. The device as recited in claim 1, further comprising:
a voltage source configured to output a voltage potential, the voltage source being configured in communication with the electrode assembly and the reference electrode;
an electrode selector configured to control the voltage source; and
a processor configured in communication with the electrode selector, the processor configured to control the electrode selector.

8. The device as recited in claim 1, wherein the drive electrode layer of each drive electrode assembly is coupled to a conductor trace.

9. The device as recited in claim 1, wherein the microfluidic channel has a height and width dimensioned to accommodate a droplet that can be introduced to an inlet of the microfluidic channel.

10. The device as recited in claim 1, further comprising:
a voltage source configured to output a voltage potential, the voltage source being configured in communication with the electrode assembly and the reference electrode; and
an electrode selector configured to control the voltage source.

11. The device of claim 1, wherein a width of the reference electrode and each of the drive electrode assemblies is about as wide as the microfluidic channel.

12. The device as recited in claim 1, wherein the surfaces of each drive electrode assembly corresponds to one or more of a square shaped electrode, a rectangular shaped electrode, a round shaped electrode, or an elliptical shaped electrode.

13. The device as recited in claim 12, wherein a width of the reference electrode and each of the drive electrode assemblies is about as wide as the microfluidic channel.

14. The device as recited in claim 1, in which the microfluidic channel ranges in length from about 0.5 mm to about 50 mm, in height from about 1 µm to about 5 mm and in width from about 10 µm to about 5 mm.

15. The device as recited in claim 1, wherein the reference electrode ranges in depth from about 100 nm to about 10 µm.

16. The device as recited in claim 1 wherein the drive electrode assembly ranges in length from about 10 µm to about 1 mm and in width from about 10 µm to about 5 mm, the height of the drive electrode layer ranges from about 10 nm to about 1 µm, the height of the intermediate dielectric layer ranges from about 1 nm to about 1000 nm and the height of the first and second stationary phase layers range from about 1 µm to about 1 mm.

17. The device as recited in claim 1, wherein the channel is filled with water.

18. The device as recited in claim 1, further comprising a heater configured and arranged so as to be effective to provide heat to the microfluidic channel.

19. The device as recited in claim 1, wherein:
two of the drive electrode assemblies define a gap; and
the gap is filled with an electrically insulating material.

20. The device as recited in claim 1, wherein the microfluidic channel has a cross-section with a shape that is at least one of square, rectangular, elliptical, racetrack, oval, diamond, hexagonal, circular, and concentric circles.

21. An analytical system comprising:
a microfluidic channel device including a microfluidic channel configured to receive and move a droplet including at least two analytes, the microfluidic channel device comprising:
  a substrate including a substrate surface;
  an array of drive electrode assemblies disposed upon the substrate surface, the drive electrode assemblies being arranged along a path, each drive electrode assembly including:
    a drive electrode layer including a first drive electrode surface configured in contact with the substrate surface and including a second drive electrode layer surface,
    a dielectric layer including a first dielectric layer surface configured in contact with the second drive electrode surface and including a second dielectric layer surface, and
    at least one of the drive electrode assemblies includes a first stationary phase layer including a first stationary phase layer surface configured in contact with the second dielectric layer surface and including a second stationary phase layer surface, the first stationary phase layer comprising a first material configured to partition a first analyte from the droplet as the droplet is moved over the first stationary phase layer, so that at least some of the first analyte is separated from the droplet and the at least some of the first analyte remains partitioned in the first stationary phase layer when the droplet is moved from the first stationary phase layer;
  an optically translucent plate including a plate surface;
  a reference electrode facing the second stationary phase layer surface of the drive electrode assemblies and separated from the substrate surface by a distance defining the microfluidic channel;
  wherein at least one of the array of drive electrode assemblies includes a second stationary phase layer including a first stationary phase layer surface configured in contact with the second dielectric layer surface and including a second stationary phase layer surface, the second stationary phase layer comprising a second material, different from the first material, the second material configured to partition a second analyte from the droplet as the droplet is moved over the second stationary phase layer, so that at least some of the second analyte is separated from the droplet and the at least some of the second analyte remains partitioned in the second stationary phase layer when the droplet is moved from the second stationary phase layer, and where the second analyte is different from the first analyte;
  a voltage source configured to output a voltage potential, the voltage source being configured in communication with the electrode assembly and the reference electrode; and
  an electrode selector configured to control the voltage source;
a light source configured to direct a beam of light incident upon the first and second stationary phase layers;
wherein the stationary phase layers are configured to receive the beam of light and generate reflected light; and
a spectrometer configured to collect and analyze the reflected light from the stationary phase layers.

22. The analytical system as recited in claim 21, further comprising an advancing mechanism, the advancing mechanism configured to sequentially position successive drive electrode assemblies in a path of the beam of light.

23. The analytical system as recited in claim 21, further comprising a plurality of the microfluidic channel devices arranged in communication with one another.

24. The analytical system as recited in claim 23, wherein the plurality of microfluidic channel devices are arranged such that the droplet may be branched from one of the microfluidic channel devices to another of the microfluidic channel devices.

* * * * *

UNITED STATES PATENT AND TRADEMARK OFFICE
CERTIFICATE OF CORRECTION

PATENT NO. : 8,734,628 B2  
APPLICATION NO. : 12/720755  
DATED : May 27, 2014  
INVENTOR(S) : Casasanta, III Page 1 of 1

It is certified that error appears in the above-identified patent and that said Letters Patent is hereby corrected as shown below:

On the Title Page, Item [56], under "OTHER PUBLICATIONS", in Column 2, Line 1, delete "editition," and insert -- edition, --, therefor.

On Title Page 2, Item [56], under "OTHER PUBLICATIONS", in Column 2, Line 21, delete "Mlcrofluid" and insert -- Microfluid --, therefor.

In the Specification

Column 1, Line 39, delete "is side" and insert -- is a side --, therefor.

Column 1, Line 42, delete "is side" and insert -- is a side --, therefor.

Column 3, Line 66, delete "1 μn;" and insert -- 1 μm; --, therefor.

Column 4, Line 27, delete "polyacrylimide," and insert -- polyacrylamide, --, therefor.

Column 4, Line 43, delete "affinity" and insert -- affinity. --, therefor.

Signed and Sealed this  
Twenty-third Day of September, 2014

Michelle K. Lee  
*Deputy Director of the United States Patent and Trademark Office*